United States Patent [19]
Jacobsen et al.

[11] Patent Number: 6,056,734
[45] Date of Patent: May 2, 2000

[54] METHOD FOR AUTOMATIC DOSING OF DRUGS

[75] Inventors: Stephen C. Jacobsen; Gaylen M. Zentner, both of Salt Lake City, Utah

[73] Assignee: Sarcos LC, Salt Lake City, Utah

[21] Appl. No.: 09/097,950

[22] Filed: Jun. 16, 1998

Related U.S. Application Data

[63] Continuation-in-part of application No. 08/797,296, Feb. 7, 1997, Pat. No. 5,782,799.
[51] Int. Cl.[7] ........................................................ A61K 9/22
[52] U.S. Cl. .......................................... 604/891.1; 604/131
[58] Field of Search ............................... 604/890.1, 891.1, 604/19, 20, 22, 23, 65, 67, 244, 246, 137, 138, 140, 145, 148, 90, 89; 623/24, 25, 93

[56] References Cited

U.S. PATENT DOCUMENTS

| | | |
|---|---|---|
| 3,840,009 | 10/1974 | Michaels et al. . |
| 3,923,060 | 12/1975 | Ellinwood, Jr. ........................... 128/260 |
| 4,312,347 | 1/1982 | Magoon et al. . |
| 4,326,522 | 4/1982 | Guerrero et al. . |
| 4,425,117 | 1/1984 | Hugemann et al. . |
| 4,439,197 | 3/1984 | Honda et al. . |
| 4,457,752 | 7/1984 | Vadasz . |
| 4,564,363 | 1/1986 | Bagnall et al. . |
| 5,167,625 | 12/1992 | Jacobsen et al. . |
| 5,196,002 | 3/1993 | Hanover et al. . |
| 5,603,354 | 2/1997 | Jacobsen et al. . |
| 5,607,691 | 3/1997 | Hale et al. ................................ 424/449 |
| 5,618,269 | 4/1997 | Jacobsen et al. . |
| 5,773,019 | 6/1998 | Ashton et al. ........................... 424/423 |
| 5,773,422 | 6/1998 | Komer ...................................... 514/30 |
| 5,851,547 | 12/1998 | Fujioka et al. ........................... 242/426 |

*Primary Examiner*—Wynn Wood Coggins
*Assistant Examiner*—Deborah Blyveis
*Attorney, Agent, or Firm*—Thorpe, North & Western LLP

[57] ABSTRACT

The method for automatic dosing of drugs utilizes a microdelivery device which may be implanted in or otherwise administered to an animal or human. A microdelivery device is configured to have at least one compartment containing at least one drug so that a plurality of doses of the drug(s) are held within the device. In accordance with the present invention, the microdelivery device selectively actuates a compartment to selectively release doses of the drug(s) to provide an efficacious dosing pattern. One primary function of the present invention is to release two or more pesticides in such a pattern that parasites are effectively controlled while preventing the development of tolerance to the drugs within the parasites. Preferably, the microdelivery device is programmable to effectuate the release of the drug(s) at a desired time to maintain efficacious levels of the drug while minimizing the amount of drug which must be used.

35 Claims, 9 Drawing Sheets

METHOD FOR AUTOMATIC DOSING OF DRUGS

This is a continuation-in-part of U.S. application Ser. No. 08/797,296 filed Feb. 7, 1997 and subsequently issued as U.S. Pat. No. 5,782,799 on Jul. 21, 1998.

BACKGROUND OF THE INVENTION

1. Field of the Invention

The present invention relates to a method of automatic dosing of drugs. More particularly, the present invention relates to a method for using electromechanical mechanisms and micromachines for dosing of drugs to maximize the effectiveness of the drugs and to prevent the development of drug tolerance and resistance.

2. State of the Art

It is well known in the fields of animal husbandry and veterinary medicine that it is usually desirable and often necessary to treat farm animals with drugs for parasites. The parasites of concern will often vary depending on the farm animal concerned and may include both ectoparasites and endoparasites. To eliminate or control these parasites, farm animals are often sprayed with or fed parasiticides, injected with these drugs or sprayed with drugs which act as parasite repellents. To accomplish such control of the parasites, the farm animals typically must be rounded up and placed in a holding area so that each animal may be properly dosed with the drug(s). Once treated, the animal is released until the next dosing is required.

Unfortunately, rounding up the animals each month, etc., is time consuming and expensive. The animal must be located and then brought to a suitable location for administration of the drug. Because of the time and expense involved with such round-ups, the farmer is forced into a compromise of overdosing the animal with a very large dose of the drug to prolong the period during which the drug is present at levels which meet or exceed the minimum effective level, thereby decrease the frequency with which the drugs must be administered, or accepting the expense of frequent round-ups to repetitively dose the animals. For example, a topically applied drug may have an efficacy threshold which relates to a 750 milligram dose of a given medication. However, to extend the period between dosing, a significantly larger dose is typically used. In FIG. 1, there is shown a curve indicating a normal, exponentially declining (i.e., first-order) efficacy curve where the drug is provided by prior art diffusion devices, such as ear tags, at a very high initial dose in order to maintain drug levels above the efficacy threshold for a prolonged period.

Referring to FIG. 1, the initially high drug level 10 that is available early in the treatment period is typically much higher than the efficacy threshold 20. In the present example, the initially high drug level 10, is 3,750 milligrams, a drug level that would require a dose which is at least four to five times higher than the efficacy threshold for the drug used. Such large doses create several problems and negatively impact the animal by causing host toxicity, decreased weight gains, and loss of income to the animal handlers/owners An additional problem with the initial high dose is that high levels of the drug may still be present should the farmer desire to slaughter the animal within the time period correlated with the upper portion, indicated at 30, of the first-order declining kinetic curve. The high, persistent drug levels can limit the farmer's marketing response and potentially lead to adverse reactions in consumers.

In the FIG. 1 example, the drug, assumed to be a parasiticide for discussion purposes, which has been diffused onto/into the animal remains above the efficacy threshold for approximately 90 days. Once the amount of drug present falls below the efficacy threshold, the drug is present in insufficient amounts to adequately kill the targeted parasites. However, it is well known that the prolonged presence of subtherapeutic levels of a drug gives rise to the development of resistance to the drug within the targeted parasites. In a resistant parasite population, the efficacy threshold is shifted upward substantially. Therefore, due to use of prior art diffusion controlled dosage forms, numerous previously beneficial antibiotics and parasiticides are now of limited effectiveness because the target microbes and parasites have developed sufficient resistance to the drug to withstand even very high dosages that the host animal cannot tolerate. Drugs that are not biocides also are negatively impacted by this type of dosing pattern as manifested by enzyme down regulation and the clinical development of tachyphylaxis.

There have been numerous attempts to overcome these concerns. For example, it has been proposed to implant in farm animals devices which provide for the release of drugs at a time other than implantation. Examples of such devices are included in the U.S. Pat. Nos. 4,564,363, 4,326,522, 4,425,117, 4,439,197, 3,840,009, 4,312,347 and 4,457,752. Unfortunately, these devices tend to be expensive to use, typically they allow only for a one time (continuous) discharge of a single drug, and are otherwise disadvantageous. Thus, there is a need for a method of administering drugs which overcomes the disadvantages of the prior art.

SUMMARY OF THE INVENTION

It is an object of the present invention to provide an improved method for dosing animals/humans which requires only a single application to the animal/human during a treatment period.

It is another object of the present invention to provide such a method which prevents or substantially reduces the development of drug resistance.

It is still another object of the present invention to provide a method which maintains an efficacious dose of the drug within the animal/human throughout the treatment period.

It is yet another object of the present invention to minimize the amount of drug necessary to stay above the drug's efficacy threshold by providing dosing events which are accurate and precise.

It is still yet another object of the present invention to enable the user to control the amount of the drug present in the animal's/human's system to thereby enable the user to increase drug levels during traditionally high periods of disease or parasitic challenge.

Yet another object of the present invention is to provide such a method which provides electronic control over drug delivery, rather than depending on the chemical attributes of the drug being delivered.

Still yet another object of the present invention is to provide such a method which is independent of the drug.

Additional objects of the invention include the use of electromechanical devices which may be used topically, ruminally or implanted, and which may be used in both human and animal applications.

The above and other objects not specifically enumerated are realized in specific illustrated embodiments of a method for automatic repetitive dosing of a single drug or alternate dosing of two or more drugs including an electromechanical microdelivery system which has at least one container for holding at least one drug to be dosed and which is attached to, implanted in, or orally administered to the animal/human. The electromechanical microdelivery system is programmed to release an initial dose of the drug to the recipient. The initial dose is then followed by periodic doses of the drug or drugs to achieve an efficacious treatment of the recipient.

In accordance with one aspect of the invention, the first dose is administered to the recipient and the amount of drug is allowed to diminish in, for example, a first-order kinetic decline. Of course, those skilled in the art will appreciate that the present invention applies equally well to any type of decreasing drug concentration.

Before the drug is allowed to pass below the known efficacy threshold for the drug, the electromechanical microdelivery system releases another dose of the drug or an initial dose of another drug sufficient to bring the amount of the at lease one of the drugs in/on the recipient above the efficacy threshold for that drug. In a situation where a first and a second drug are being dosed, the dosing of the first and second drugs are cycled to achieve a desired efficacy by always maintaining at least one of the drugs above the efficacy threshold for that drug. This repetitive dosing approach maintains high-level efficacy with a minimum drug exposure for the host animal and the environment. For example, the first and second drugs may be administered shortly before the other drug drops below the efficacy threshold, or several doses of the first drug may be provided with an occasional dose of the second drug, or several doses only of the first drug may be provided.

In accordance with another aspect of the present invention, the first and second drugs are delivered in such a manner that each drug remains present in the body in amounts above the efficacy threshold, or, the two drugs may be alternated to ensure that at least one of the drugs is always well above the efficacy threshold without introducing excessive amounts of either drug into the animal.

In accordance with yet another aspect of the present invention, the electromechanical microdelivery system could be used to supply a plurality of different drugs with any desired sequence and timing during a designated period. Thus, for example, antibiotics or parasiticides could be delivered monthly as described above and other drugs, such as hormones which stimulate animal growth, could also be provided. The use of the electromechanical microdelivery system allows a farmer to provide all of the medication needs for an animal for a prolonged period of time with a single administration of the programmed electromechanical microdelivery system. Such a method can save considerable amounts of time and money by avoiding repetitive handling of the animals, avoiding doses which may induce toxicity in the host, and maximizing efficacy with minimal drug doses.

In accordance with still another aspect of the present invention, the amount of drug delivered during each dose may be correlated with the amount of drug required to address particularly high or low disease patterns. Thus, for example, the amount of drug provided by a dose may be increased or subsequent doses may be delivered more frequently during periods, such as spring or summer, when parasitic infestations may be particularly common, and decreased to a level slightly above the efficacy threshold during fall and winter or other periods when parasite infestations are not as common.

In accordance with still yet another aspect of the invention, a plurality of different drugs for humans and animals may be automatically dosed during different periods. For example, concerns may be present about the use of two drugs because of their proclivity to interact and produce undesirable side effects. With the method of the present invention, a first drug may be delivered and allowed to fall below levels at which it is likely to interact with the second drug. The second drug may then be administered and allowed to fall to a sufficiently low level before the first drug is reintroduced. Thus, medical personnel can ensure that a patient has his or her medication administered at appropriate times without requiring the medical personnel to be present each time one of the drugs is administered. Accurate, precise delivery of complex dosing regimens is thus achieved in an unattended and automatic fashion, eliminating patient compliance and practitioner administration errors from the overall therapeutic outcome.

Still another aspect of the invention includes introducing the initial dose of a drug and allowing the drug to diminish, for example, in a first-order kinetic decline. Before the drug is allowed to pass below the efficacy threshold which has been established, the electromechanical microdelivery system releases a second dose of the drug to maintain the amount of the drug in the patient above the efficacy threshold for the drug.

The electromechanical microdelivery system is sufficiently small that it may be administered either topically, ruminally, or it may be implanted. If necessary, the dosages provided by the electromechanical microdelivery system may be maintained within a single compartment for each dose, or larger doses may be achieved by using two or more compartments.

Still yet another aspect of the present invention is mixing two or more drugs within a compartment, or during application to achieve a desired balance of the two drugs which is available to the patient The two drugs disposed in a single compartment may be selected to synergistically interact with each other, or may be simply selected on the basis that dosing of the two drugs is desirable at approximately the same time. When dispensed from separate compartments, the drugs will typically interact in a symbiotic manner to further improve the efficacy of the method of the present invention.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various aspects of the present invention will be described so as to enable one skilled in the art to make and use the invention. It is to be understood that the following description is only exemplary of the principles of the present invention, and should not be viewed as narrowing the pending claims.

Figure 1:
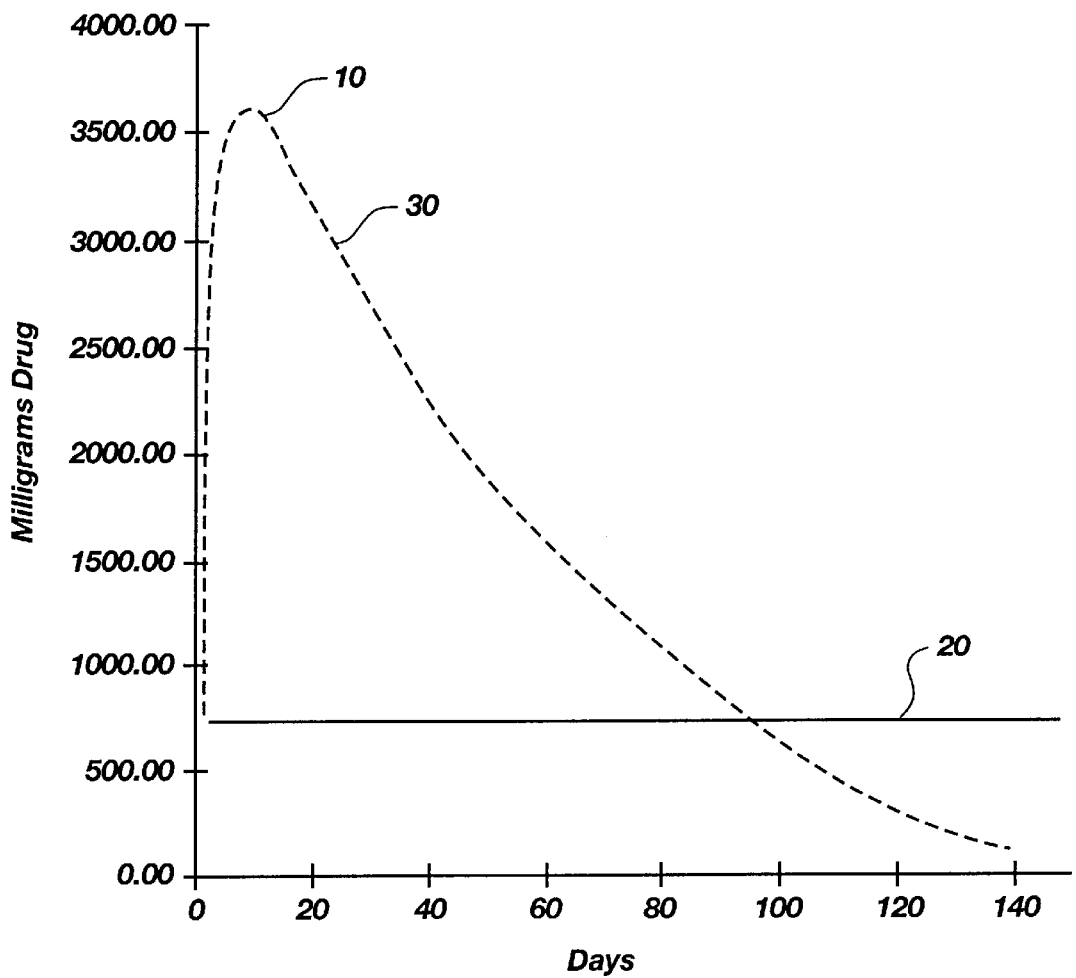
FIG. 1 shows a graph demonstrating a first-order kinetic decline of drug levels in/on an animal when the drug is delivered by a device that releases drug by the conventional diffusion method.
Figure 2A:
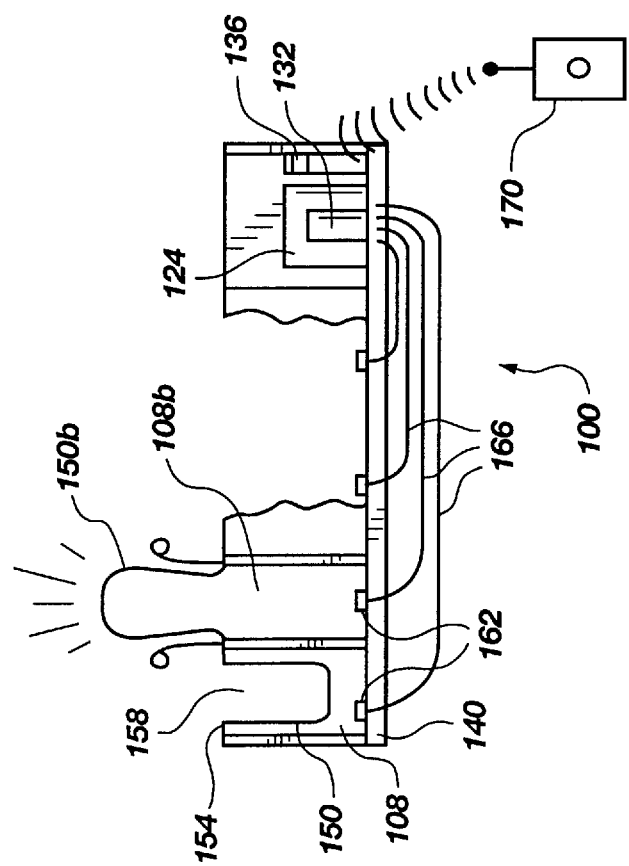
FIG. 2A shows a fragmented, side cross-sectional view of the electromechanical microdelivery system of FIG. 2.
Figure 2:
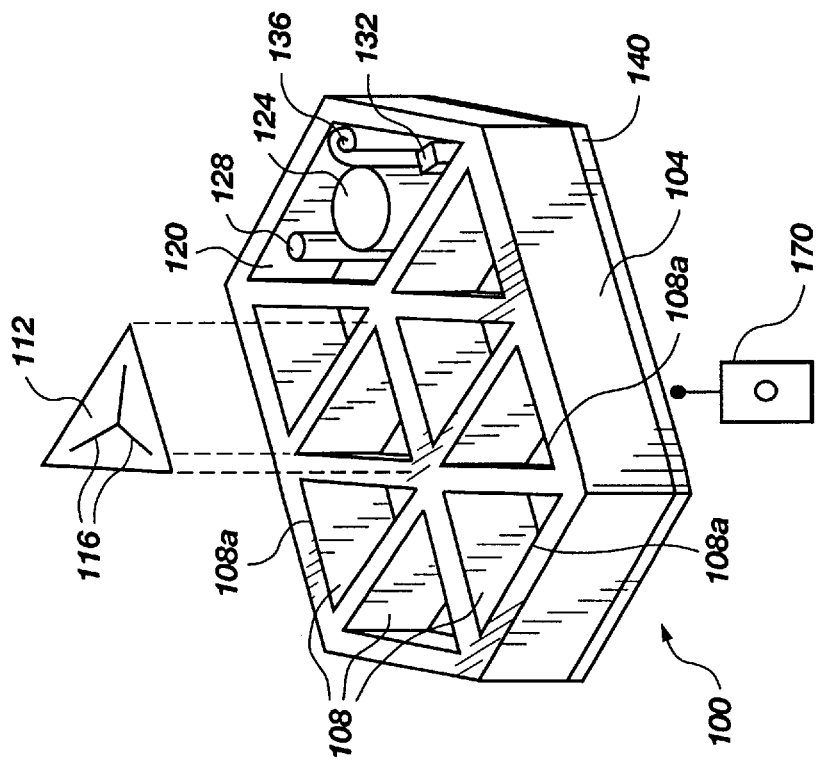
FIG. 2 shows a perspective view of an electromechanical microdelivery system which may be used to practice the method of the present invention.

Referring to FIGS. 2 and 2A, there is shown an electromechanical microdelivery system, generally indicated at 100, which may be used to practice the teachings of the present invention. The electromechanical microdelivery system 100 includes a housing 104 having a plurality of compartments 108 formed therein. Each of the compartments 108 has an open upper end 108a, over which a rupturable or removable cap 112 is placed. The caps 112 may be attached to the housing 104 so that one or two sides rupture when desired, or a plurality of score lines 116 can be made so that the cap 112 opens when forcefully contacted by medication disposed therein.

As shown in FIG. 2, the compartments 108 are arranged in rows to achieve maximum dosing volume in a minimum space. Positioned at one end of the two rows of compartments 108 is a utility compartment 120. The utility compartment 120 is used to house a battery 124, an oscillator 128, and a timing circuit 132. A receiver and antenna 136 may also be provided. The battery 124, the oscillator 128, the timing circuit 132 and the receiver/antenna 136 (if provided) are mounted on a substrate 140 which forms a floor of the utility compartment 120 and the other compartments 108.

Disposed in each compartment 108 is a drug containment sack 150 shown in FIG. 2A. The drug containment sack 150 has an upper opening 154 and a void 158 disposed within the sack 150 for holding medication. The upper opening 154 of each drug containment sack 150 is attached adjacent the opening 108a of a corresponding compartment. The drug containment sacks are provided for holding a drug dose to be delivered to an animal to which the drug delivery system is administered. The drug dose may be formulated as solids such as tablets, powders and granules, semisolids such as ointments and creams, or even solutions, suspensions, and emulsions.

The drug containment sacks will typically be made of material which is flexible and chemically inert. The exact material used to form the sack may vary depending on the drug to be administered. Several likely materials are set forth in U.S. Pat. No. 5,167,625, which is expressly incorporated herein.

Disposed at the bottom of each compartment 108 on the substrate floor 140 is a pyrotechnic gas generating element, typically a bead of material 162 which is responsive to heat resulting from an electrical signal applied to a heating element, thereby igniting and producing gas that fills and pressurizes the corresponding compartment. Alternatively, a non-toxic foam may be produced by an ignition material to similarly fill a corresponding compartment 108. As a compartment 108 fills with gas, the gas forces the corresponding drug containment sack 150 upwardly and the sack, in turn, forces the drug formulation contained therein against the cover 112 which ruptures and allows the drug formulation to be expelled as the sack everts. Sack 150b of FIG. 2A is shown fully everted from compartment 108b which ensures that all drug formulation initially contained in the sack, i.e. a dose, is administered to the patient.

The pyrotechnic gas generating material 162 might illustratively be a composition of nitrocellulose, nitroglycerine, hydrazine, or polyvinyl nitrate. Although not shown, a second or more pyrotechnic gas generating beads might also be included in each compartment to be activated after the first bead has been activated to thereby better ensure the complete release of drug formulation from each compartment.

The oscillator 128 (FIG. 2) supplies an oscillatory signal to the timing circuit 132 which is adapted to selectively connect the battery 124 to the pyrotechnic gas generating beads 162 in some preferred order (to activate the beads) and with a predetermined delay between activation of the different beads, to thereby discharge and administer doses of drug formulation to the patient (animal or human) over a period of time.

The timing circuit 132 operates in such a manner to selectively and sequentially connect the battery 124 by way of electrical conductors 166 to the pyrotechnic gas generating beads 162, While shown as being disposed underneath the substrate 140, the conductors can also be disposed in or on top of the substrate. Thus, the timing circuit is able to selectively trigger the release of numerous doses of therapeutic drugs over a prolonged period of time, For example, half of the compartments 108 could be filled with a first insecticide and the other half filled with a second insecticide. The timing circuit 132 could be programmed to activate release from a compartment having the first insecticide, and then activate release from a compartment containing the second insecticide after some predetermined delay. If necessary, a dose could be provided by the actuation of two or more compartments.

In such a manner, a single administration of the electromechanical microdelivery system 100 can deliver a series of medication doses over a prolonged period of time. For example, if a parasiticide were released monthly, a single administration of the electromechanical microdelivery system 100 would enable treatment of an animal for eight full months. Prior to the present invention, farmers would typically either round up their animals monthly to administer the medication, or would use a diffusion device which results in initially dangerously high drug exposures, followed by a prolonged period of sub-therapeutic levels as the drug diffusion device is depleted. Additionally, diffusion controlled devices are often problematic because the chemical structure and reactivity of the drug to be delivered can significantly impact the delivery curve.

The present invention offers the advantages of periodic administration of the drugs from a one time administration of the dosage form. The chemical structure of the drugs will have no effect on dosing because the microdelivery device 100 does not rely on drug diffusion or other drug-associated physicochemical phenomena to control the drug release pattern. Thus, considerable product development cost savings are achieved, in addition to improved drug efficacy.

Still another advantage of the method of the present invention is that the user can control when the electromechanical microdelivery system 100 begins to administer the initial dose. A transmitter 170 can be provided to remotely transmit signals to the receiver and antenna 136. Signals from the transmitter 170 activate the timing circuit 132, thereby allowing the timing circuit to cause the drugs to be administered in a manner desired by the user. Thus, for example, a rancher could administer two electromechanical microdelivery systems to each of his cattle, each of the electromechanical microdelivery systems containing a six-month supply of antibiotics. One of the electromechanical microdelivery systems would be activated to begin release of the antibiotics shortly after implantation. The other electromechanical microdelivery system 100 could be activated approximately six months later by the transmitter 170. Thus, the rancher could reap the benefits of a one-year dosing regimen of antibiotics from a single administration of the dosage form. Likewise, an initial dose of a vaccine could be disposed in one electromechanical microdelivery system activated shortly after implantation with another electromechanical microdelivery system containing a booster for the vaccine activated at some later point in time when such a booster is desired or necessary. Annual administration of medication would save large amounts of time and money, by reducing animal handling and increasing the efficacy of the drugs. This method also provides a prolonged treatment period that can markedly exceed the duration of traditional diffusion devices, while eliminating concerns of host toxicity, subtherapeutic drug levels, development of parasite resistance, and tachyphylaxis.

The electromechanical microdelivery system can be formed into numerous different embodiments. For example, in FIG. 3 there is shown an electromechanical microdelivery system, generally indicated as 200, having an elongate tubular housing 204. Formed in the housing is a central compartment or vesicle 208, and a plurality of other vesicles 212 disposed in a circle about the central vesicle as shown. The vesicles 208 and 212 extend along a substantial length of the housing 204 generally in parallel with one another and include openings at the upper end 204a of the housing. A cover 216 with a plurality of rupturable portions 216a is disposed over the upper end 204a of the housing 204 to cover the openings of the vesicles, but to also rupture and allow discharge of the contents of a vesicle when adequate pressure is supplied to the cover from inside the vesicle. Although the vesicles 212 are shown to be generally the same size, different size and shape vesicles could be provided to allow for delivery of different amounts of a drug.

The housing 204 also includes a bottom compartment 220 in which are disposed a battery 224, an oscillator 228 and a timing circuit 232. The compartment 220 is separated from the vesicles 208 and 212 by a floor or substrate 236 in which are located a plurality of pyrotechnic gas generating beads 240. The circuit components 224, 228 and 232 selectively and successively ignite the pyrotechnic gas generating beads 240 in the same manner as discussed for the embodiment of FIG. 2.

Disposed in each vesicle 208 and 212 near the bottom thereof are pistons or plungers 244. The side surfaces of the plungers 244 are shaped to conform to and snugly fit within the side walls of the corresponding vesicles so that as a plunger is forced upwardly in a vesicle by gas pressure, it pushes out of the housing a drug formulation contained in the vesicle. The plungers 244 are forced upwardly in the corresponding vesicles by the activation of the pyrotechnic gas generating beads (or other geometric shapes) 240. Of course, the plungers 244 need not be used, as the drug formulation can be forced out the vesicle 208 by the gas itself.

Advantageously, the plungers 244 are made of polyurethane, synthetic rubber, silicone greases, petrolatum, paraffin, beeswax or other material which will allow for a slidably tight fit within the vesicles. The housing 204 could illustratively be made of rigid molded polymers (polycarbonate, ABS, polyesters, or other nonelastomeric thermoplastics or thermosets) or formed metals.

The electromechanical microdelivery system 200 is advantageous in that the large number of vesicles 208 and 212 can hold numerous doses of the medications to be administered. For example, if alternating dosages are desired on a monthly basis, the electromechanical microdelivery system 200 could provide drugs for more than a year without the need for implanting or otherwise administering additional dosage forms.

Other electromechanical microdelivery systems may also be employed to administer drugs in a manner in accordance with the method of the present invention.

For example, the volumetric pump described in U.S. Pat. No. 5,603,354 to Jacobsen et al., assigned to the assignee of the present invention, and herein incorporated by this reference, may be utilized. Likewise, the pressure-driven attachable topical fluid delivery system disclosed in U.S. Pat. No. 5,618,269 and the piston-actuated attachable topical fluid delivery system described in U.S. application Ser. No. 08/434,463 both to Jacobsen et al. may be employed to deliver the drug(s) in accordance with the present invention.

Figure 4:
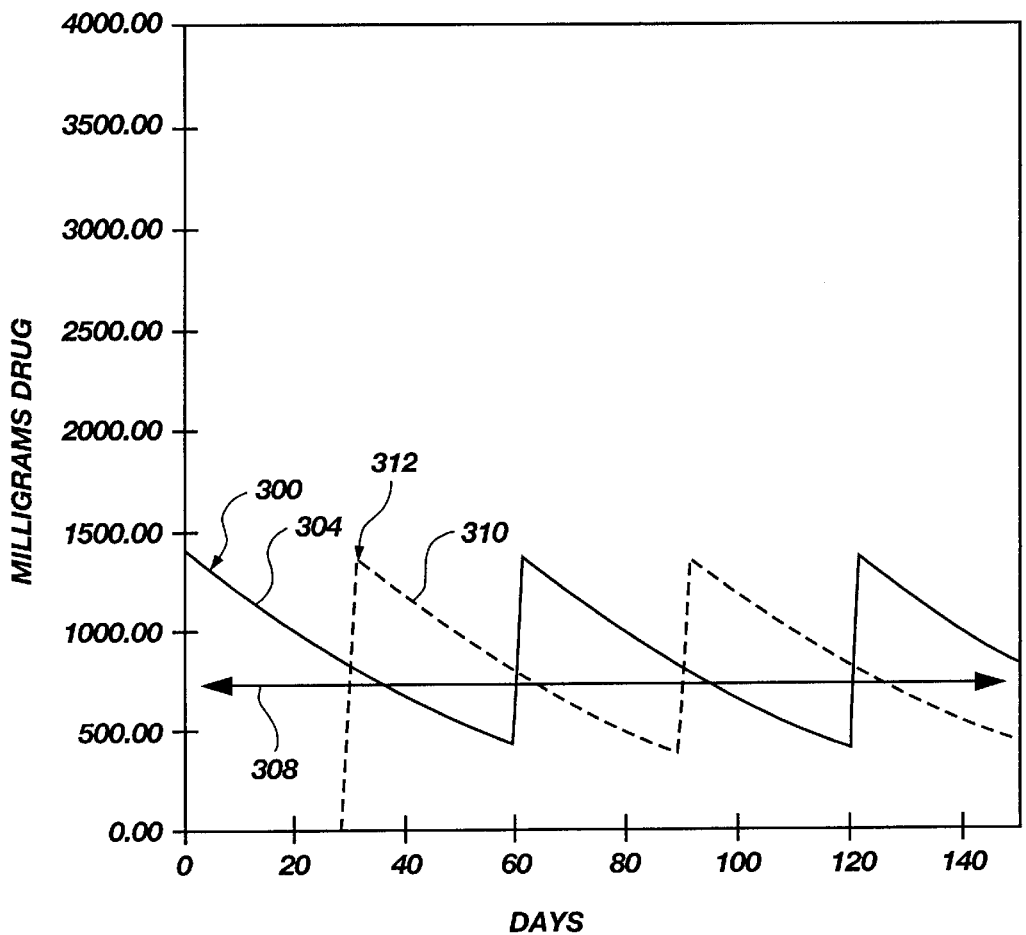
FIG. 4 shows a graph demonstrating a method of repetitive, alternating dosing in accordance with the principles of the present invention, along with a first-order kinetic decline for the delivery of each dose.

Referring now to FIG. 4, there is shown a graph demonstrating a method of dosing in accordance with the principles of the present invention, along with a first-order kinetic decline after delivery of each dose. For illustration purposes, the amount of drug available on an ear tag device configuration that is available to kill flies is graphed.

An initial dose 300 of a first drug, represented by solid line 304, is provided to kill flies. While referred herein as an ear tag which is clamped to an animal's ear, those skilled in the art will appreciate that the devices could be implanted, placed in the stomach of the animal, or placed in other areas. Additionally, the reference to a first drug should not be viewed as to limit the contents of a compartment of the microdelivery device, as two or more drugs could be disposed in a compartment of the microdelivery device for simultaneous administration.

As shown in FIG. 4, the initial dose is about 1400 milligrams. However, those skilled in the art will appreciate that the amount provided will depend both on the drug used, the type and size of the animal, and the disease. For illustration purposes, treatment of a parasitic fly infestation will be discussed, as those skilled in the art will be familiar with numerous parasiticides which may be used for such a purpose. After approximately 30 days, the levels of the first parasiticide 304 drop to near the efficacy threshold 308. Rather than providing additional quantities of the first drug 304, the electromechanical microdelivery system (FIG. 2 or FIG. 3) is programmed to activate expulsion of a second drug 310 from a compartment or vesicle to provide the dosage indicated at 312. As shown in FIG. 4, 1400 milligrams of the second drug are provided to kill any parasites which have not been killed by the first drug 304.

As the second drug 310 falls toward the efficacy threshold 308, a sufficient quantity of the first drug 304 is again provided by the electromechanical microdelivery system to bring the levels of the first drug 304 back up to 1400 milligrams. The amount of the first drug 304 necessary to reach the target dose is less than needed for the initial dose because of the residue first drug from the first dose. Thus, the second and subsequent dosings of either drug can typically be in smaller quantities, or delayed a sufficient period of time to prevent drug build up to levels which risk host toxicity. As shown in FIG. 4, approximately 900 milligrams is used for each dose after the initial dose for each drug.

By cycling the drugs in the manner described, considerable advantages are achieved. Of primary importance is that the cycling prevents the development of resistance to the parasiticide in the targeted parasite. There is always at least one of the drugs which is sufficiently above the efficacy threshold to eliminate the parasitic infestation. The two cycling drugs prevent multigenerational parasite turnover in the presence of subtherapeutic drug levels which is typically associated with development of resistance to drugs. Thus, resistance is substantially eliminated.

An additional advantage of the cycling is that the repetitive replenishment of drug keeps the total drug exposure for the host to a minimum. As shown in FIG. 4, one device administration has provided effective treatment of the animal for approximately five months. To achieve a similar treatment pattern with conventional dosage forms such as prior art diffusion devices would require the farmer, rancher, etc., to round up and treat the animal with the first or second drugs during each of the five months or periodically reapply diffusion-type devices. When dealing with large numbers of animals, the time and expense involved with such procedures is prohibitive.

Figure 4A:
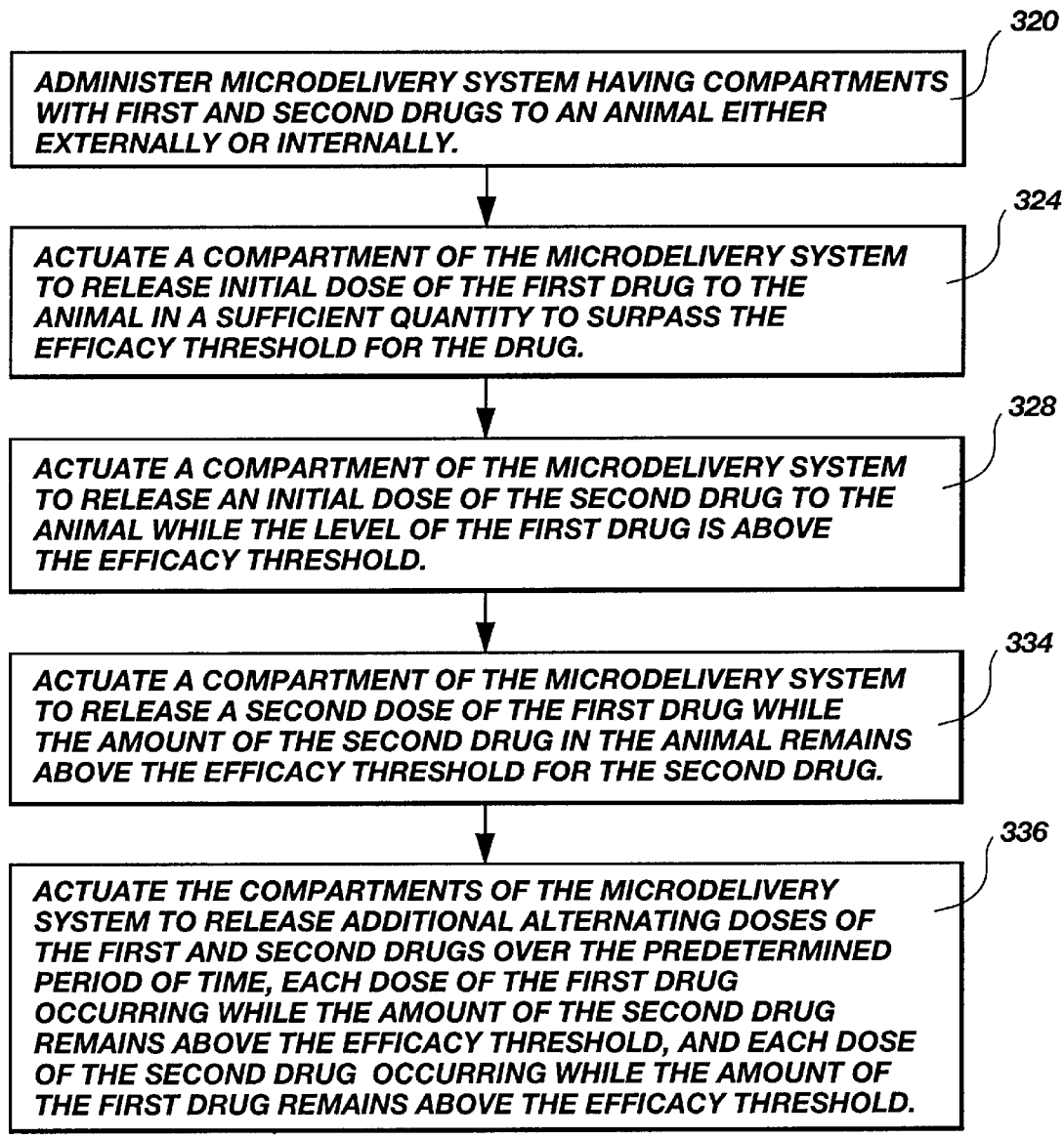
FIG. 4A shows a flow chart of the process used for implementing the dosing method demonstrated by the graph of FIG. 4.

FIG. 4A shows a flow chart of the process used for implementing the dosing method demonstrated by the graph of FIG. 4. The initial step 320 is accomplished by administering the device to the animal. The device may be attached to a collar, ear tag or similar device to provide topical treatments, or may be conveniently implanted, such as in an animal's ear or orally administered for retention in the rumen of ruminant animals, to provide the drugs into the blood stream.

The second step 324 is accomplished by providing an initial dose of the first drug in a sufficient quantity to surpass the efficacy threshold for the drug. This is followed by the third step 328 of providing an initial dose of the second drug while the level of the first drug is above the efficacy threshold.

The fourth step 334 is performed by supplying a second dose of the first drug while the amount of the second drug in the animal remains above the efficacy threshold for the second drug. Those skilled in the art will appreciate that the efficacy thresholds for the first and second drugs will often be different. However, for ease of reference, the efficacy thresholds for the two drugs are shown to be the same.

As indicated at 336, the dosing pattern can continue for a predetermined period of time, such as for 6 months. The actual time during which the electromechanical microdelivery system will typically be used depends on the parasite infestation patterns and the amount of the first and second drugs which may be held in the electromechanical microdelivery system.

While the graph of FIG. 4 shows the first and second drugs alternatingly falling below their efficacy thresholds, those skilled in the art will appreciate that a desirable dosing pattern is to keep both drugs above their efficacy thresholds for the entire period of treatment Thus, instead of alternating the first and second drugs on a monthly basis, dosing may occur on a biweekly basis or a larger dose may be supplied. Such a dose, however, will be well below the potentially dangerous doses which attend administration of diffusion-type devices.

While more compartments are used if biweekly dosing is selected, the overall quantity of each drug used is relatively similar because the second and subsequent dose of each drug will need to be substantially less to bring the drug level to that shown at the top of each first-order kinetic curve.

EXAMPLE 1

In accordance with the graph and flow chart of FIGS. 4 and 4A, permethrin and chlorpyrifos insecticides are disposed in the electromechanical microdelivery system 100 of FIGS. 2 and 2A and attached as an ear tag onto the ear of an animal for control of ectoparasites such as horn flies. The insecticides are formulated in combination with solvents, polymers and other additives as necessary to retard depletion of an expelled dose over a one-month period. A first dose of permethrin is supplied in sufficient quantity to raise the amount of available permethrin above the efficacy threshold. Applying a first-order kinetic depletion curve to the amount of permethrin that is available, the permethrin is formulated to stay above the efficacy threshold for one month. Similarly, the electromechanical microdelivery system 100 is programmed to release a sufficient quantity of chlorpyrifos to bring the level of the drug above the efficacy threshold for chlorpyrifos and maintain a level above the efficacy threshold for one month. The electromechanical microdelivery system 100 actuates a compartment holding the largest dose of chlorpyrifos four weeks after the first dose of permethrin is released.

Four weeks after the first dose of chlorpyrifos is released, the electromechanical microdelivery system again actuates a compartment containing permethrin to release additional quantities of that drug. Because of the residual quantity of permethrin from the initial permethrin dose, the second permethrin dose will be a fraction of the first permethrin dose. According to FIG. 4, the second permethrin dose would be approximately 65% of the initial permethrin dose. Therefore, the electromechanical microdelivery system will be programmed as to which individual compartment to release for the first and all subsequent doses.

By continuing to alternate doses of the first and second drugs until each of the eight compartments 108 has been emptied, the electromechanical microdelivery system 100 provides doses which prevent parasite infestations for approximately six months. This is accomplished with a single device administration, saving the farmer or rancher time and money, while allowing both drugs to be kept well below levels which might induce host toxicity. Additionally, tolerance development by the parasites is nearly eliminated because the continual replenishment and alternating of the pesticides precludes multigenerational parasite turnover under conditions of sub-lethal insecticide exposure that is required for tolerance to develop. It is important to recognize in accordance with the present invention that alternating, as used herein, may include a one to one sequence, e.g. A-B-A-B . . . , or some other combination, e.g. A-A-B-A-A-B-A-B-B . . . , as may be desired to most efficaciously minimize the threat of parasite, etc., and infestation during a predetermined period of time, while minimizing the risk of toxicity to the animal.

Figure 5:
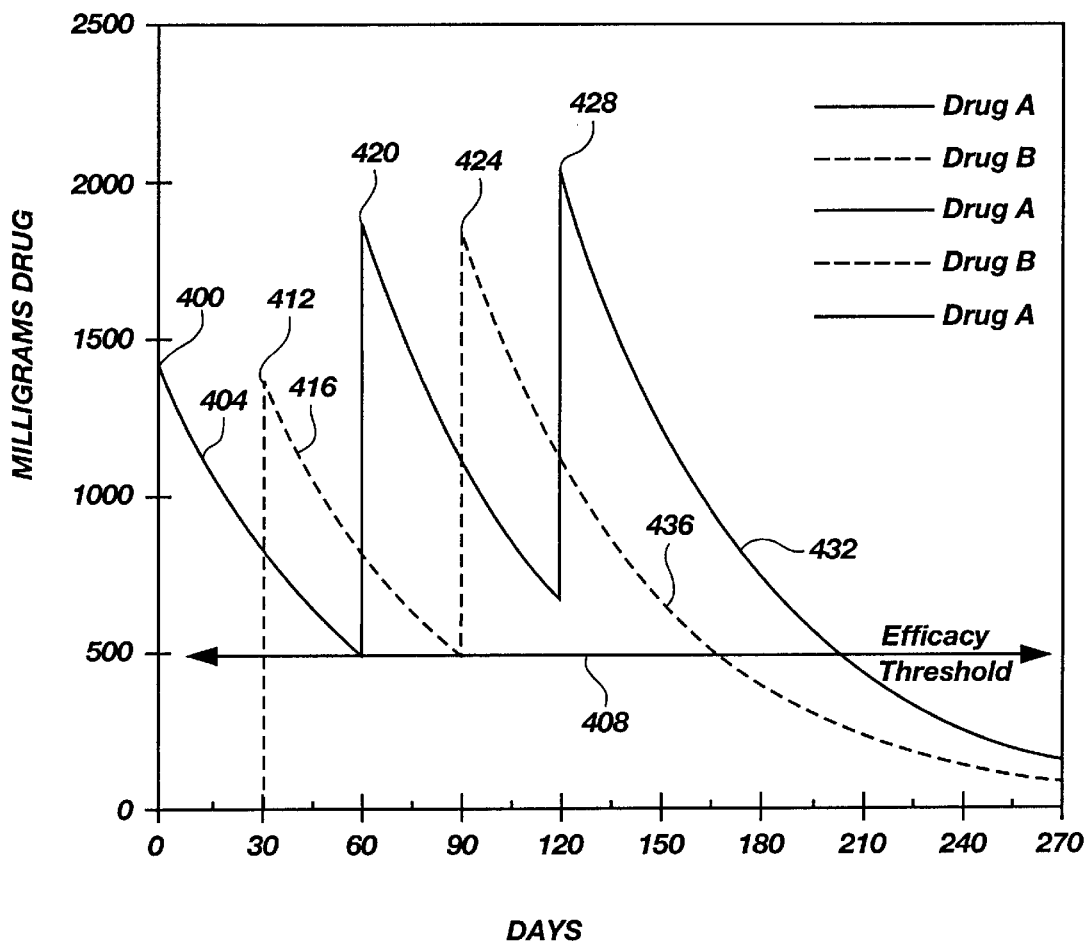
FIG. 5 shows graph of another dosing procedure in accordance with the present invention.

Referring now to FIG. 5, there is shown a graph of another dosing procedure in accordance with the present invention. An initial first dose 400 is provided of a first drug, the level of which is indicated by line 404. The initial first dose 400 of the first drug is approximately 1400 milligrams. At such a quantity, the amount of the first drug on the animal or available on a device configuration such as an ear tag, remains above the efficacy level 408 for approximately 60 days.

Approximately one month after the first drug is released, an initial dose 412 of a second drug, indicated by the dashed line 416, is released. The amount of the second drug 416 which is released is also 1400 milligrams and will take approximately 60 days to drop below the efficacy threshold for the second drug. For ease of reference, the efficacy threshold for the second drug is indicated as being the same as the efficacy threshold 208 for the first drug. Those skilled in the art will appreciate that the efficacy threshold for each drug used must be considered when determining the quantity of that drug released and the time between dosing and the presence of subtherapeutic levels of the drug.

Unlike the dosing regimen in FIG. 4, the amount of drug delivered with each dose is kept the same. Thus, because the level of the first drug has fallen to 500 milligrams, providing a second dose of 1400 milligrams, as indicated at 220, results in 1900 milligrams of therapeutically available drug. Likewise, a similar increase in the level of the second drug is achieved by use of a full 1400 milligram dose of the second drug, indicated at 424.

FIG. 5 also shows a third dose, indicated at 428, of the first drug. The third dose 428 is also 1400 milligrams, thereby bringing the amount of the first drug to a peak of slightly more than 2000 milligrams. Each of the two drugs are eliminated or degraded with a first-order kinetic decline, as indicated at 432 for the first drug and 436 for the second drug.

The dosing of the drugs so as to create an increase in the drug level in the animal with each subsequent dose can be used advantageously in several ways. First, if the goal is simplicity in manufacturing the electromechanical microdelivery system, the method allows the system to be manufactured with each compartment containing the first drug to have the same quantity. Likewise, each compartment containing the second drug can have the same quantity. Rather than requiring the electromechanical microdelivery system 100 or 200 to be programmed to release the compartment with the first (higher) dose of each drug, the system must only ensure that the compartments containing the first and second drugs, respectively, are released in an alternating pattern. To prevent build-up of the first and second drugs, all doses after the second dose for each drug would simply be delayed.

In the alternative, the escalating quantity achieved by the dosing level as shown in FIG. 5 can be used to improve the correlation between dosing and infestation patterns. For example, if a particular parasite infestation is most common during a specific month or period, the electromechanical microdelivery system can be programmed to release a compartment containing a particularly high quantity of one or both drugs during the infestation period. Doses subsequent to the infestation period would be modified to return the drugs to a level desired when high-level infestation is not a concern.

Of course, a single drug could be used in the dosing pattern. As will be apparent to those skilled in the art from FIG. 5, either of the drugs delivered could be administered periodically to keep the drug doses to a minimum while ensuring that the available amount of the drug remains above the efficacy threshold. In such a manner, the development of resistance would be greatly diminished, as the available amount of the drug remains above the subtherapeutic level needed for resistance to develop.

Figure 3:
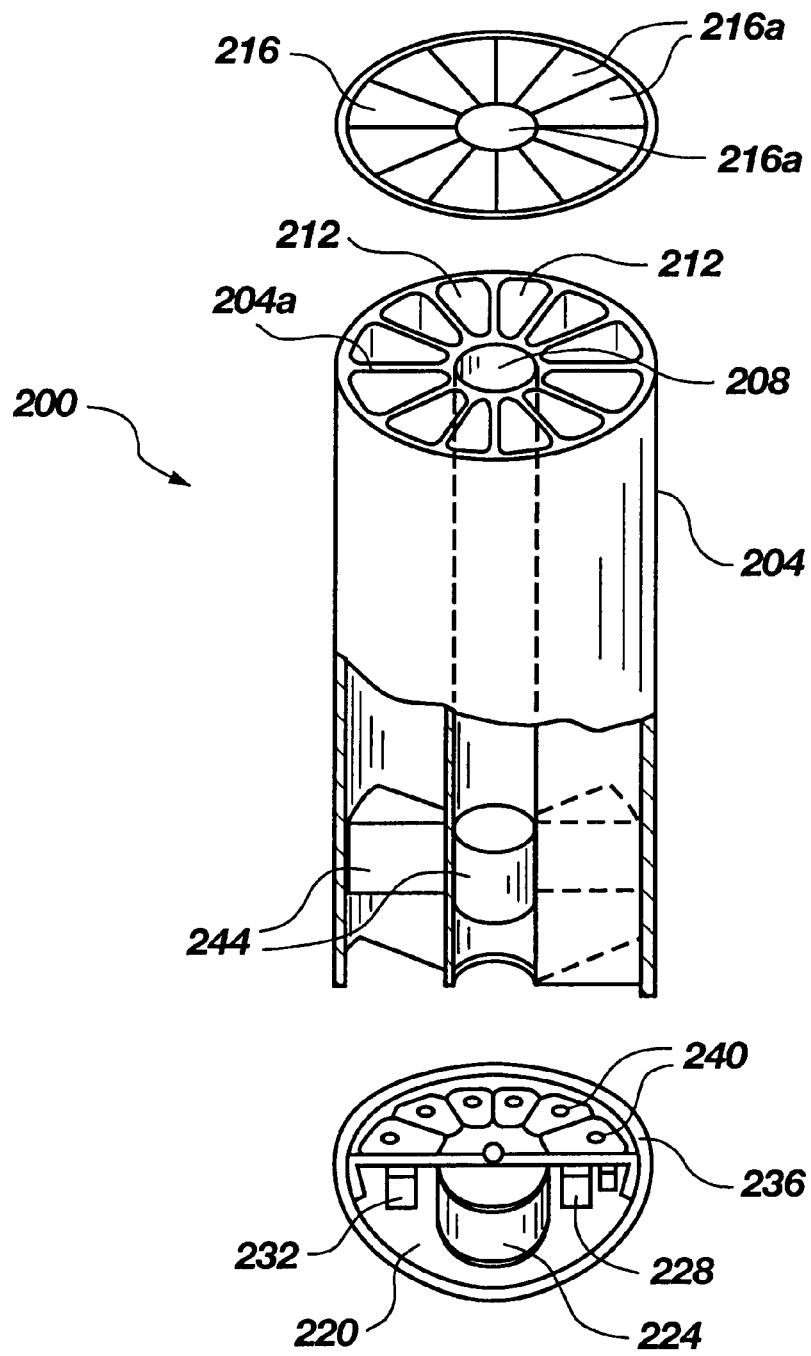
FIG. 3 shows an isometric, exploded, partially cutaway view of an alternate embodiment of an electromechanical microdelivery system which may be used in accordance with the teachings of the present invention.
Figure 5A:
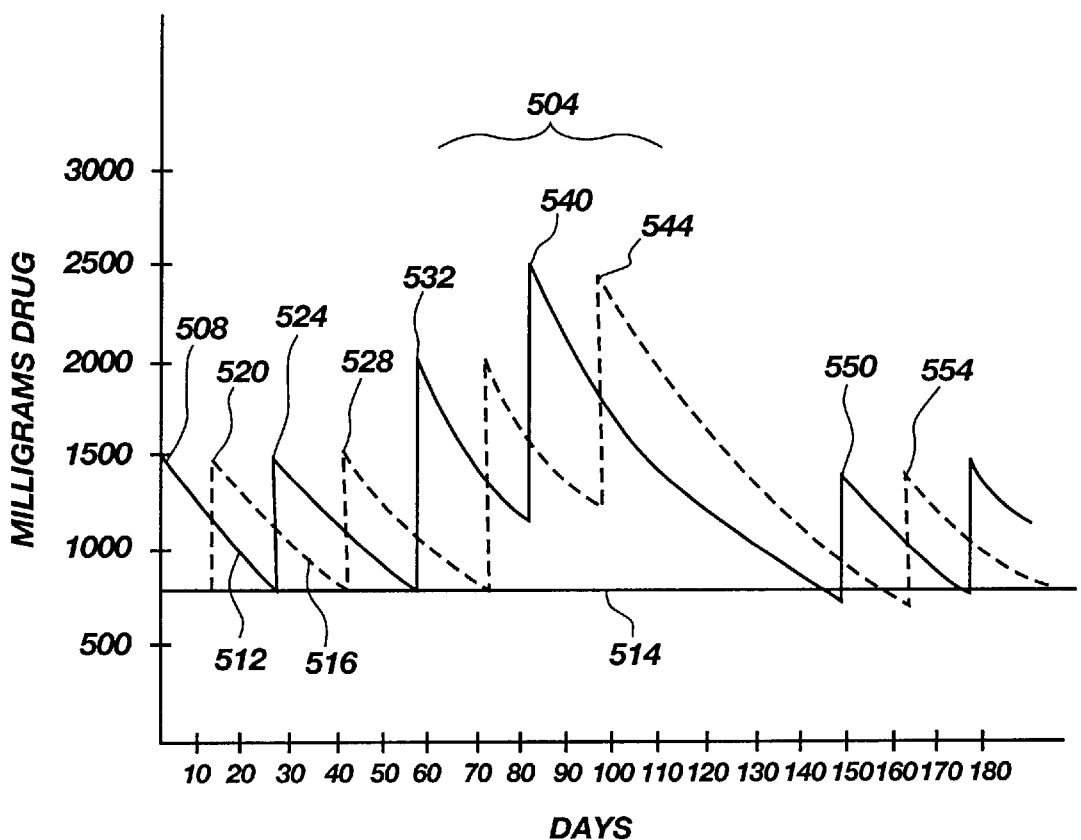
FIG. 5A shows another graph of a dosing procedure performed in accordance with the present invention.

Referring now to FIG. 5A, there is shown a graph representing the use of a microdelivery device such as those shown in FIGS. 2 through 3. The device is used to selectively control the therapeutically available amount of each drug to correlate the same to an infestation period, indicated at 504. An initial dose 508 of a first drug, indicated by the solid line 512 is 1400 milligrams and the efficacy threshold 514 for the first drug is 700 milligrams Thus, the first drug 508 falls to the efficacy threshold 514 after approximately 30 days.

A second drug, indicated by dashed line 516 is provided. The initial dose 520 is 1400 milligrams and the second drug 516 has a similar efficacy threshold 514 as the first drug. The initial dose 520 of the second drug 516 is provided approximately 15 days after the initial dose 508 of the first drug 512.

A second dose 524 of the first drug 512 is provided after thirty days. To achieve an available level of 1400 milligrams for the first drug 512, the second dose 524 is 700 milligrams.

On about the forty-fifth day, a second dose 528 of the second drug 516 is provided. The second dose 528 of the second drug 516 is also 700 milligrams, thereby bringing the available level of the second drug back up to approximately 1400 milligrams, A third dose 532 of the first drug 512 is provided on the 60th day. Because the 60th day is also the approximate beginning of the typical infestation period 504 for a particular parasite, the third dose 532 of the first drug 512 is increased to 1400 milligrams, the same as the initial dose 508. The third dose of the first drug 512 achieves a level of approximately 2100 milligrams. The increase in drug level decreases the risk that the animal will become infested during a high-level infestation period.

The second drug 516 is also released in a greater amount during its third dose 536 to raise its level to approximately 2100 milligrams. The level for each of the drugs is raised up to approximately 2450 milligrams by providing a 1400 milligram fourth dose 540 and 544 for the first and second drugs, respectively.

To return to the preinfestation drug levels, the fifth dose 550 and 554, for each of the drugs is spaced approximately 60 days from the fourth doses 540 and 544 of the respective drug. It is important to note that while the first drug transiently falls below the efficacy threshold, the second drug remains fully therapeutic and covers the need. In addition, as illustrated in FIG. 5A, each drug level drops approximately 50% every 30 days. Thus, for example, the dose 540 brings the level of the first drug to 2450 mg on day 80, which falls to approximately 1225 mg on day 110, and to approximately 612 mg on day 140. The fifth dose 550 for first drug 512 is 790 milligrams, as is the fifth dose 554 for the second drug 516. Any subsequent treatment is provided by doses of 700 milligrams.

Thus, it can be seen that the method for using the electromechanical microdelivery system 100 or 200 enables the user to control dosing patterns to correlate available drug levels with infestation patterns. By careful planning, the user is able to administer the minimum amount of the drug to maximize efficacy. This can be achieved either by timing the release of each compartment to achieve desired dosing levels, or by adjusting the quantity of the first or second drug which is contained in each compartment and then actuating the delivery from the compartments in a predetermined pattern. When a first quantity of one of the drugs is delivered in the initial dose, maintaining the effective levels of the drug can either be done by applying a second, smaller quantity on the second and subsequent dose for that drug, or by providing the same dose and extending the time before the next delivery. Likewise, the delivered drug levels can be modulated to correspond with seasonal fluctuations in parasitic infestations by altering either the quantity of the drugs delivered and/or by changing the timing at which the drugs are delivered.

While discussed primarily with respect to the control of parasites in animals, those skilled in the art will appreciate that the present method has a variety of medical applications. Thus, for example, a microdelivery device 100 or 200 could be programmed to provide medications in patterns which maximize their efficacy while minimizing adverse reactions or other problems. Furthermore, because the microdelivery devices are implantable or attachable to the patient, the drugs may be delivered in the most efficacious cycling while allowing the patient relative mobility. Thus, the principles of the present invention are equally applicable to medical applications in humans as it is to parasite control in animals.

Figure 6:
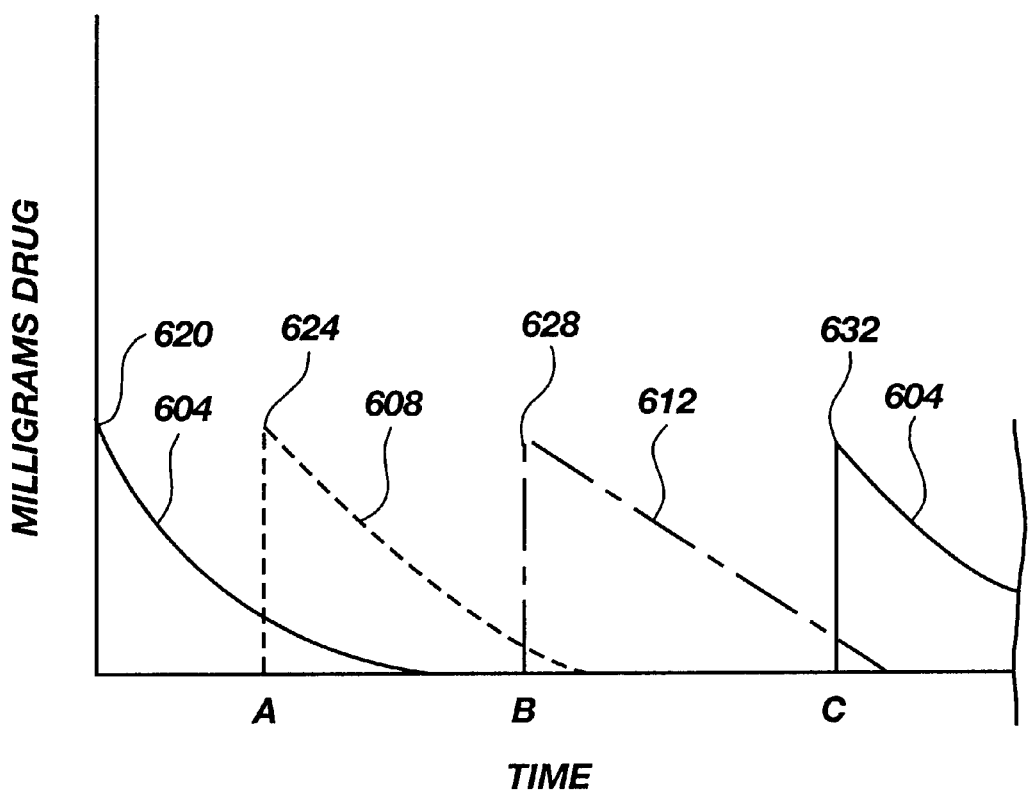
FIG. 6 shows a graph of yet another dosing procedure performed in accordance with the present invention.

Referring now to FIG. 6, there is shown an alternate dosing procedure of the present invention. Each of three drugs 604, 608 and 612 are provided to an animal. However, if two or more of the drugs are simultaneously present in sufficient quantities, the animal being treated will suffer from adverse side effects. Those skilled in the art will appreciate that the type and extent of any side effects are dependant on the amount of drugs provided.

To prevent adverse side effects, the first drug 604 is supplied to the animal in an initial dose 620. Based on the dose provided, it is known that the systemic level of the first drug 604 will fall to a level at which the second drug 608 may be introduced without side effects after time period A. Thus, the electromechanical microdelivery system 100 (FIGS. 2 and 2A) or 200 (FIG. 3) is programmed to release an initial dose 624 of the second drug 608 after time period A.

Following a first-order kinetic curve, the second drug 608 falls to a sufficiently low level after time period B to allow introduction of an initial dose 628 of the third drug 612. The third drug 612 also is eliminated until a second dose 632 of the first drug 604 may be introduced at time period C. The alternate dosing of the first, second, and third drugs 604, 608 and 612, respectively, can be continued until the drug delivery is no longer needed, or until the electromechanical microdelivery system 100 or 200 has been fully depleted.

Figure 7:
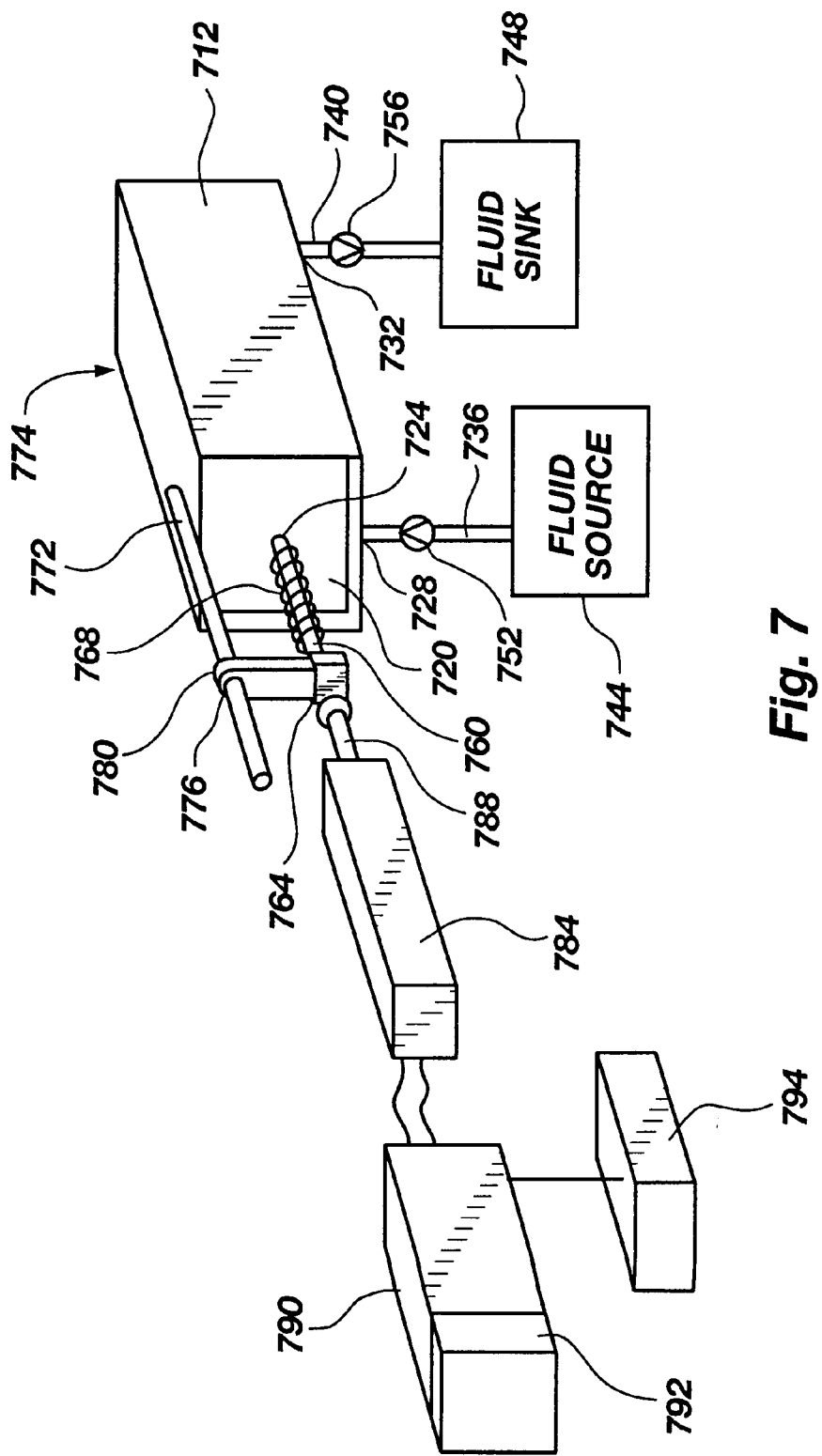
FIG. 7 is a perspective view of another electromechanical microdelivery system which may be used to practice the method of the present invention.

The use and application of an electromechanical microdelivery system, such as the electromechanical micropump disclosed in U.S. Pat. No. 5,603,354 as herein described and incorporated by reference, may be employed in accordance with the method of the present invention. FIG. 7 illustrates a perspective view of a volumetric pump disclosed in U.S. Pat. No. 5,603,354 which includes a generally elongate housing 774, formed with an elongate cavity therein. The housing 774 might illustratively be formed with an exterior shell 712 made of metal or hard plastic, and an interior filler disposed against the shell 712, with the cavity formed centrally therein. The filler could similarly be metal or hard plastic.

Disposed in one end of the housing 774 is a resilient sheet of material 720 made, for example, of latex rubber, silicone rubber, or nitride rubber. The sheet of material 720 fills the end of the housing 774 to prevent communication between the outside of the housing and the cavity except through an aperture 724 positioned in line with the cavity.

An inlet duct 728 is formed in the housing 774 generally adjacent to the sheet of material 720, to communicate with the cavity, and an outlet duct 732 is similarly formed in the housing to communicate with the cavity at the other end thereof. Conduits 736 and 740 respectively couple ducts 728 and 732 to a fluid source 744 and a fluid sink 748. Check valves 752 and 756 are disposed respectively in conduits 736 and 740 to allow fluid to flow from the fluid source 744 into the cavity and prevent the reverse flow, and to allow fluids to flow from the cavity to the fluid sink 748 and prevent the reverse flow. The fluid source 744 could be any source of fluid which it is desired be pumped to fluid sink 748, such as an IV administration set which includes a bottle of fluid to be administered to a patient, with the fluid source 744 being the bottle and the fluid sink 748 being the patient receiving the fluid. Of course as will be evident upon further discussion, the fluidic pump could be used in a variety of environments.

An elongate shaft or plunger 760 is disposed in the aperture 724 of the sheet of material 720 to extend at least partially into the cavity of the housing 774. The shaft 760 may have a circular cross section and have a somewhat smaller circumference than that of the cavity so that the shaft may be moved in a reciprocating fashion back and forth in the aperture 724 and cavity. The aperture 724 is preferably shaped similarly to the cross-sectional shape of the shaft 760 and is preferably the same or slightly smaller in size in order to completely surround and grip the shaft to form a sphincter seal and prevent fluid from escaping the cavity. As the aperture is formed in the resilient sheet of material 720, the aperture conforms to the shape of the shaft 760 even if their shapes are not identical though it will be obvious to those skilled in the art that the more the shapes differ the less effective the seal will be.

Disposed on the free end of the shaft 760 is a bumper pad 764. A coil spring 768 is disposed about that portion of the shaft 760 which is outside of the housing to provide a bias force against the bumper pad 764 to urge the shaft outwardly from the housing.

A support rod 772 is mounted on the top of the housing 774 and extends forwardly therefrom, and a stopper finger 776 is slidably mounted on the rod 772 so that it may be slid forwardly or rearwardly along the rod. A set screw 780 is provided in the stopper finger 776 to allow for setting or fixing the position of the stopper finger on the rod. Stopper finger 776 extends downwardly to a position in the pathway of possible movement of the bumper pad 764 to prevent the bumper pad and thus the shaft 760 from moving outwardly from the housing 774 beyond the location of the stopper finger. The bumper pad 764 rests against the lower end of the stopper finger 776 to illustrate that the bumper pad 764 and shaft 760 are prevented from moving any further outwardly from the housing 774. The setting of the stopper finger 776 by means of the set screw 780 determines the stroke or excursion of movement of the shaft 760 within the cavity of the housing 774.

A driving mechanism 784, such as a solenoid or motor, is positioned in front of the housing 774 so that a solenoid drive core 788 extends toward the bumper pad 764 as shown. When the drive mechanism 784 is activated (for example by applying an electrical current to a solenoid), the driver core 788 is caused to move towards the bumper pad 764, engage it and move the bumper pad and the shaft 760 toward the housing 774 so that the shaft moves further into the cavity of the housing. When the drive mechanism 784 is deactivated, the drive core 788 retracts into the drive mechanism 784 allowing the coil spring 768 to urge the bumper pad 764 and thus the shaft 760 outwardly from the housing until the bumper pad contacts the stopper finger 776. Alternative activation and deactivation of the drive mechanism 784 will thus result in the shaft 760 being reciprocated within the cavity of the housing 774.

In operation, when the shaft 760 is moved further into the cavity, any fluid within the cavity is forced into the conduit 740 and through the check valve 756 to the fluid sink 748. When the shaft is allowed to retract or move outwardly of the cavity, a negative pressure is created in the cavity, causing fluid to be drawn from the fluid 744 through the check valve 752 and into the cavity. The continued reciprocation of the shaft 760 thereby provides for pumping fluids from the fluid source 744 to the fluid sink 748.

EXAMPLE 2

In this example, the electromechanical microdelivery system, such as pump 774 illustrated in FIG. 7, automatically delivers a maintenance dose of 10 to 200 microliters per day of the ectoparasiticide permethrin, formulated as a 60% w/w solution in methyl carbitol or other solvent, onto the fur and skin of dogs or cats. The microliters delivered per day are determined by the size of the animal and the susceptibility of the parasites in question. In most cases fleas and ticks are the target parasites. The maintenance dose is selected to provide high level parasite control with a minimum amount of parasiticide. On a previously untreated animal, it is frequently desirable and advantageous to provide an initial loading dose on the first day of treatment. Loading doses typically vary between 100 and 1500 microliters. The loading dose rapidly raises the parasiticide level on the host animal into the lethal range, thus providing rapid kill of the offending parasite(s) and providing rapid relief to the host animal. The maintenance dose then maintains sufficient levels of the parasiticide to control the infestation at an acceptable level (>80 % efficacy is typically desired) for a prolonged period of several weeks up to one year. Sufficient drug for the loading dose and all maintenance doses is contained within a reservoir container from which the electromechanical microdelivery system dispenses the programmed doses.

EXAMPLE 3

The use and application of an electromechanical microdelivery system, such as the electromechanical micropump illustrated in FIG. 7 as herein described and incorporated by reference, in the long-term, unattended topical delivery of parasiticides for the control of both ectoparasites and endoparasites is disclosed. In this preferred embodiment, the parasiticide is a combination of permethrin and ivermectin dissolved in an appropriate solvent such as methyl carbitol, Dowanol, or hexylene glycol. The permethrin is present at a 60% w/w concentration and the ivermectin at a 1 % w/w concentration. The combination formulation is dosed as disclosed in Example 2; however, the spectrum of target parasites is expanded to include both ectoparasites (e.g., fleas and ticks) and endoparasites such as the tissue stage of *Dirofilaria immitis* larvae which is ultimately responsible for lethal heartworm disease. Although some susceptible types of gastrointestinal worms would also be controlled by this formulation, improved control of gastrointestinal worms (e.g., hookworms, roundworms, and whipworms) would be achieved by substituting milbemycin oxime for the ivermectin. Due to the exquisite sensitivity of *Dirofilaria immitis* to the ivermectin and milbemycin classes of parasiticides, 100% control of *Dirofilaria immitis* is achieved. The electromechanical micropump drug delivery system relieves the animal handler from frequent manual dosing and assures that doses are given at the proper time and in the proper amount. This provides for uninterrupted drug coverage for the animal and eliminates the possibilities for parasite infestation that inevitably accompany human errors in manually administering frequent and repetitive doses.

EXAMPLE 4

In this example, the electromechanical microdelivery system is used to automatically administer the anticoagulant enoxaparin sodium for prevention of deep vein thrombosis which may lead to pulmonary embolism. The electromechanical micropump is programmed to deliver 0.6 ml/day of a sterile solution containing 60 mg of enoxaparin sodium. The drug is administered subcutaneously in two divided doses through either an indwelling catheter or freshly inserted small gauge hypodermic needle. Typically, the doses are spaced every twelve hours. Sufficient drug solution is contained in the attached drug reservoir for 2 to 6 doses (1 to 3 days) depending on local medical protocol for change-out of infusion sets. Once the reservoir is exhausted, the entire assembly is discarded and a new assembly is positioned and switched on. The duration of use of a given drug delivery device is presently limited by the potency period of the indwelling catheter. As advances occur in indwelling catheter technology that permit longer duration catheter use, the drug delivery technology is fully capable of unattended use for periods of several months. The automation of parenteral anticoagulant drug delivery using small, lightweight, inexpensive electromechanical micropumps that provide instrument level precision and accuracy permits patients to leave high-cost hospital environments and return home without compromising the quality of therapy.

EXAMPLE 5

The administration of proteinaceous thrombolytic agents that enzymatically decompose unwanted thrombi and emboli (i.e., blood clots), is readily accomplished with the electromechanical micropump. The dosing requirements of three clinically useful thrombolytic agents in the treatment of potentially life-threatening coronary thrombi or pulmonary emboli are listed in the following table:

| Disease | Thrombolytic Agents | | |
| --- | --- | --- | --- |
| | urokinase | streptokinase | TPA |
| coronary thrombi: (direct coronary artery infusion via catheter) | 4 ml/min 2 hrs | 10 ml stat -then- 1 ml/min 1 hr | 6 ml/min 1 min -then- 1 ml/min 54 mins -then- 0.33 ml/min 2 hrs |
| pulmonary emboli: (iv infusion) | 1.5 ml/min 10 mins -then- 0.25 ml/min 12 hrs | 0.5 ml/min 30 mins -then- 0.1 ml/min 24 to 72 hrs | 0.83 ml/min 2 hrs |

In all cases the drug reservoir is filled with a solution of the desired thrombolytic agent. The electromechanical micropump then delivers the solution from the reservoir at preprogrammed rates that match the specific indications within the table. With all of these drugs, the required delivery rates are low and of short duration, yet in most cases require timed modifications as the therapeutic regimen progresses. Electromechanical micropumps that are preprogrammed will assure delivery of the correct dosing regimen for a given drug, reduce the possibilities for practitioner errors, and substantially accelerate initiation of therapy in emergency situations. Utilization of the electromechanical micropump also extends thrombolytic therapy to field situations where paramedics and other emergency medical personnel can reliably initiate therapy in transit to the hospital

EXAMPLE 6

In this example, an electromechanical micropump or other electromechanical microdelivery system is employed for delivery of drugs and beneficial agents that require parenteral administration over a prolonged period. These drugs are chemically classified as proteins, peptides, oligonucleotides, and DNA. Examples of drugs within these chemical classes are vaccines, gene therapies, and naturally occurring proteins with beneficial pharmacology that are produced by genetic engineering techniques. The electromechanical micropump is readily programmed to deliver the following common dosing regimens:

| Drug | Dosing Regimen |
| --- | --- |
| epoetin alfa (EPOGEN ™) | 0.5 to 0.7 ml every other day |
| filgrastim (NEUPOGEN ™) | 0.93 to 16.33 ml/day for 2 weeks |
| interferon alfa-2a (ROFERON-A ™) | 0.5 to 1 ml/day for 24 weeks |
| vaccines (protein antigens) | <50 µl/day for 2 to 12 weeks (continuous or combination of pulsatile with continuous pattern) |
| plasmid DNA encoding reporter genes | programmed to maximize cellular uptake of each polynucleotide |

The electromechanical micropump offers the substantial benefit of programmability to achieve an optimum response from a given drug. The small size and weight allows patients to receive sophisticated, chronic drug administration while remaining ambulatory. Patients that would often require institutionalized care would, through the use of the electromechanical micropump, be permitted to return to their home, work, or any other chosen activity.

EXAMPLE 7

In example 7, precise reduction of blood glucose levels in diabetic patients through administration of exogenous insulin is achieved by using an electromechanical micropump. Such insulin administration is required to prevent the development of the adverse effects of the disease such as blindness, organ failure, skin ulceration, and necrotic extremities requiring amputation. It is equally important, however, that the glucose levels are not reduced sufficiently to create a hypoglycemic condition that results in loss of consciousness and coma. To accomplish the needed level of control, where glucose is lowered to the proper level with no overshoot, requires monitoring of blood glucose levels many times per day with concomitant adjustment in the amount of administered insulin. Increased frequency of monitoring and dose adjustment is directly correlated with reduction in the adverse effects of the disease. The goal is to provide diabetic patients with glucose monitoring and insulin delivery devices that automatically provide continuous, feedback controlled insulin levels which in turn place the patient into a physiologically correct metabolic condition. An electromechanical micropump, such as that disclosed in FIG. 7, is a critical component in this type of closed-loop drug delivery system.

Several devices are currently available that can provide continuous monitoring of blood glucose levels. These devices operate on the principles of spectrophotometric absorption or through specific glucose chemical reactions (most being enzymatically based) occurring in small implanted probes/sensors or as part of iontophoretic transdermal devices that enhance glucose transport across skin. These monitors all provide electrical output signals that are proportional to the glucose level. The electromechanical micropump is programmed to deliver insulin in response to the level of the output signal from the monitor. The electromechanical micropump plus monitor comprise a closed-loop insulin drug delivery system that provides continuous, glucose sensitive insulin therapy that closely simulates normal physiology and substantially eliminates the ill effects of diabetes.

EXAMPLE 8

In the present example, direct infusion of chemotherapeutic agents into a tumor's arterial blood supply provides for high drug concentrations at the target tissue (i.e., tumor) while reducing the drug burden and associated undesired side effects at non-target tissues. This approach is highly beneficial in the treatment of hepatic cancers (primarily carcinomas and metastatic carcinomas originating from non-hepatic primary tumors) which are typically unresponsive to conventional chemotherapeutic approaches. An electromechanical micropump, such as that illustrated in FIG. 7, enables tumor-direct, intraarterial infusions of chemotherapeutic agents. It is desirable to deliver the chemotherapeutic agent 5-fluorouracil (5-FU) or 5-fluoro-2-deoxyuridine (5-FUdR) as continuous intraarterial infusions via the hepatic artery. When compared with conventional systemic intravenous administrations of these drugs, the direct intraarterial route improves extraction of the drug from the blood into the liver and tumor by 10 to 400-fold. This means that up to 99% of administered drug is extracted from the blood, leaving a minimal amount to enter the general circulation, and thus resulting in a marked and clinically significant reduction in the untoward effects of chemotherapy. Additionally, when administered as a slow infusion that permits the tumor to uptake the drug, it has been noted that intratumor drug concentrations are 5 to 20-fold higher than drug concentrations in surrounding normal liver tissue which indicates a preferential targeting of drug to the tumor. The electromechanical micropump would be programmed to deliver:

| Drug | Dosing Regimen |
| --- | --- |
| 5-FU | 3–30 mg/kg/day (4.2–42 ml/day) for 2 to >70 weeks |
| 5-FUdR | 0.1–0.5 mg/kg/day for 2 to >70 weeks |

A catheter is located directly into the hepatic artery and connected to the electromechanical micropump. The pump is either mounted externally with a replaceable or refillable drug reservoir, or implanted with a refillable drug reservoir. The small size of the electromechanical micropump would present few restrictions to an ambulatory patient and would allow for a high quality of life while providing therapy on an out-patient basis.

EXAMPLE 9

In this example, the entries in the following table demonstrate the utility of an electromechanical microdelivery system in parenteral delivery of antibiotics, antivirals, and antifungals. These drug agents require intravenous administration for periods of several days to several weeks, Many other drugs would similarly benefit from the electromechanical micropump, and the entries in the table do not limit or restrict the types of agents that can be administered. An electromechanical micropump, such as the electromechanical micropump illustrated in FIG. 7, provides accurate dosing of these agents while allowing the patient a normal range of activities and a high quality of life, particularly full ambulatory mobility that permits maintenance of employment and home life. The pump converts what have heretofore been drug therapies that require administration in a medical institution (e.g., hospital, clinic, or other inpatient facility), at high cost and complete loss of normal lifestyle to the patient, to low cost therapies that minimally impact the patient's daily routine.

| Drug | Dosing Regimen |
| --- | --- |
| imipenem/cilastatin | ●250 to 500 mg qid × 10 days |
| | ●pump rate: 8–16 ml/hr |
| ceftriaxone sodium | ●500 to 2000 mg bid (30 min infusion) × 14 d. |
| | ●0.4 to 1.7 ml/min for 30 mins. bid. × 14 d. |
| | NOTE: Therapy may be required for several weeks in some diseases (e.g., Lyme disease) |
| cefoxitin sodium | ●1 to 2 grams tid to qid. Or continuous infusion |
| | ●10 ml tid to 10 ml qid (30 min infusion) |
| | -or- |
| | ●30 to 40 ml/24 hrs continuous infusion |
| foscarnet | ●4 to 22 ml/hr IV infusion for 7 to 21 days |
| amphotericin B | ●6.3 to 12.6 ml/day for 1 to 8 weeks |

In the aforementioned examples, it may be desirable to implant the electromechanical micropump into the body tissue of the patient or position the electromechanical micropump on a body part such as an extremity. For example, the electromechanical micropump may be attached to the patient's arm, secured in place by either adhesives, mechanical attachment (e.g., a flexible, adjustable arm band), or a combination thereof. A drug reservoir may be connected to the electromechanical micropump inlet port through quick-connect fittings that facilitate rapid change-out once the reservoir becomes depleted. Similarly, an IV set may be connected to the electromechanical micropump outlet port. It is noted that current medical practice dictates changeout of disposable components used in parenteral drug delivery every 1 to 3 days, although longer periods between change-outs have been reported. In accordance with the present invention, it is desirable that all components be sufficiently inexpensive to be disposable, including the electromechanical micropump, if desired. Thus, the medical practitioner gains complete flexibility in the use of both the drug and the delivery device to best meet the individual needs of each patient.

Those skilled in the art will appreciate that regardless of which electromechanical microdelivery system is used, the practitioner responsible for assuring that drug therapy is provided can utilize established pharmacokinetic/pharmacodynamic principles and program the devices to deliver an optimal dosing regimen. Relying on this information, the programmer can determine not only when a drug should be released, he or she can selectively control the selected delivery system to provide different dosing levels to select an optimum dosing pattern for the particular use.

While the present invention will be desirable for a large number of insecticides, parasiticides and other drugs as listed in the Merck Index, the following drugs are currently viewed as being highly desirable for administration in accordance with the principles of the present invention which are set forth above:

chlorpyrifos
diazinon
permethrin
fipronil
lambdacyhalothrin
pyrimiphos methyl
ivermectin
doramectin
moxidectin
insect growth regulators
enoxaparin sodium
urokinase
streptokinase
TPA
epoetin alfa
filgrastim
interferon alfa-2a
vaccines
protein antigens
plasmid DNA encoding reporter genes
exogenous insulin
5-FU
5-FUdR
imipenem
cilastatin
ceftriaxone sodium
cefoxitin sodium
foscarnet
amphotericin B
acyclovir Thus, a method is disclosed for automatic dosing of one or more drugs. Those skilled in the art will recognize numerous modifications which can be made without departing from the scope and spirit of the invention. The appended claims are intended to cover the scope of the invention.

What is claimed is:

1. A method for automatic delivery of at least one drug, comprising:

selecting an electromechanical microdelivery system containing a plurality of doses of at least one drug contained within a plurality of compartments disposed therein to be administered to a patient;

administering the electromechanical microdelivery system to the patient;

programming the electromechanical microdelivery system to dispense the at least one drug to the patient according to a predetermined dosing regimen;

actuating the electromechanical microdelivery system to provide an initial dose of the at least one drug to the patient; and actuating the electromechanical microdelivery system to provide at least one other subsequent dose of the at least one drug to the patient at a predetermined time according to the dosing regimen.

2. The method of claim 1, wherein said providing an initial dose and said providing at least one other subsequent dose includes topically applying the dose to the patient.

3. The method of claim 1, wherein said providing an initial dose and said providing at least one other subsequent dose includes internally administering the doses into the patient.

4. The method of claim 1, wherein said initial dose is a loading dose of the at least one drug.

5. The method of claim 4, wherein said subsequent doses are maintenance doses of an amount less than the initial dose.

6. The method of claim 4, wherein said at least one drug is selected from a parasiticide for the control of at least one of an ectoparasite and endoparasite.

7. The method of claim 5, wherein said at least one drug is selected from is the group comprising permethrin, ivermectin and fipronil.

8. The method of claim 1, wherein said at least one drug is selected from a proteinaceous thrombolytic agent.

9. The method of claim 8, wherein said proteinaceous thrombolytic agent is selected from at least one of urokinase, streptokinase, and TPA.

10. The method of claim 1, wherein said at least one drug is selected from at least one of proteins, peptides, oligonucleotides, and DNA.

11. The method of claim 10, wherein said at least one drug is selected from the group comprising epoetin alfa, filgrastim, interferon alfa-2a, vaccines, protein antigens, and plasmid DNA encoding reporter genes.

12. The method of claim 1, further including providing a monitoring device in communication with the electromechanical microdelivery system and the patient for monitoring at least one physiological condition of the patient and for generating data representing the at least one physiological condition, and wherein said predetermined dosing regimen is automatically modified according to said data.

13. The method of claim 12, wherein said monitoring device is selected from a blood glucose level monitoring device.

14. The method of claim 13, wherein said at least one drug is comprised of insulin.

15. The method of claim 1, wherein said administering the electromechanical microdelivery system to the patient comprises locating a catheter into a hepatic artery of the patient.

16. The method of claim 15, wherein said at least one drug is selected from a chemotherapeutic agent.

17. The method of claim 16, wherein said chemotherapeutic agent is selected from the group comprising 5-FU and 5-FUdR.

18. The method of claim 1, wherein said at least one drug is selected from the group comprising antibiotics, antivirals, and antifungals.

19. The method of claim 18, wherein said at least one drug is selected from imipenem, cilastatin, ceftriaxone sodium, cefoxitin sodium, foscarnet, acyclovir, and amphotericin B.

20. The method of claim 1, wherein said electromechanical microdelivery system is an electromechanical micropump.

21. The method of claim 1, wherein said administering the electromechanical microdelivery system to the patient comprises attaching the electromechanical microdelivery system to a body part of the patient.

22. The method of claim 21, wherein said administering the electromechanical microdelivery system includes connecting an IV set to the electromechanical microdelivery system and to the patient.

23. The method of claim 1, wherein each of said subsequent doses are provided at preprogrammed intervals to ensure that a level of drug in the patient stays above a desired minimum.

24. The method of claim 1, wherein said administering comprises implanting the electromechanical microdelivery system into the patient.

25. A method for automatic alternate dosing of at least two drugs in an animal, the method comprising:

selecting an electromechanical microdelivery system having a plurality of compartments disposed therein for holding at least one drug therein;

administering the electromechanical microdelivery system to the patient;

actuating the electromechanical microdelivery system to provide a first dose of the at least one drug from a first compartment of the electromechanical microdelivery system to the patient; and actuating the electromechanical microdelivery system to provide a second dose of the at least one drug from a second compartment of the electromechanical microdelivery system to the patient at a first predetermined time after the first dose of the at least one drug according to a predetermined dosing regimen.

26. The method of claim 25, further comprising:

actuating the electromechanical microdelivery system to provide a third dose of the at least one drug at a second predetermined time after the second dose of the at least one drug.

27. The method of claim 26, wherein the method further comprises delivering additional doses of the at least one drug, each dose being spaced a predetermined period of time.

28. The method of claim 25, further comprising providing one of the plurality of compartments with a first quantity of the at least one drug and providing a plurality of the remaining compartments with a second quantity of the at least one drug which is less than the first quantity.

29. The method of claim 28, further comprising releasing the compartments having the second quantity of the at least one drug at intervals sufficiently distant from one another so that the amount of the at least one drug available to the patient is substantially the same immediately after each dose of the at least one drug.

30. The method of claim 25, further comprising providing one of the compartments with a first quantity of the at least one drug and providing a plurality of the remaining compartments with a second quantity of the at least one drug which is greater than the first quantity.

31. The method of claim 25, further comprising providing different quantities of the at least one drug in a plurality of the compartments, and wherein the method further comprises, selectively releasing the compartments to obtain a desired level of the at least one drug.

32. The method of claim 25, further comprising delivering additional doses of the at least one drug in such a manner to increase the levels of the at least one drug in the patient.

33. The method of claim 25, wherein said administering the electromechanical microdelivery system includes implanting the electromechanical microdelivery system within the patient.

34. The method of claim 25, wherein said administering the electromechanical microdelivery system includes topically attaching the electromechanical microdelivery system to the patient.

35. The method of claim 25, wherein said providing a first dose of the at least one drug is in sufficient quantity to exceed an efficacy threshold of the at least one drug for patient, and said providing a second dose of the at least one drug is in sufficient quantity to exceed the efficacy threshold of the at least one drug for the patient while the level of the first dose remains above the efficacy threshold of the at least one drug.

* * * * *